United States Patent [19]

Hoehn et al.

[11] 4,421,852

[45] Dec. 20, 1983

[54] PRODUCTION OF HIGH FRUCTOSE SYRUP FROM INULIN INVOLVING ULTRAFILTRATION

[76] Inventors: Ernst Hoehn, 128 Traverse Ave., Winnipeg, Manitoba, Canada, R2H 2G9; Curtis J. McKay, Apt. 424, 99 Dalhousie Dr., Winnipeg, Manitoba, Canada, R2G 2G5; E. Donald Murray, 833 Kilkenny Dr., Winnipeg, Manitoba, Canada, R3T 4Y4

[21] Appl. No.: 406,178

[22] Filed: Aug. 9, 1982

[30] Foreign Application Priority Data

Sep. 15, 1981 [CA] Canada .................................. 385954

[51] Int. Cl.³ .................... C13D 3/16; C13K 11/00; C12P 19/14
[52] U.S. Cl. ........................................ 435/99; 127/30; 127/43; 127/54; 435/105; 435/276
[58] Field of Search .......................... 435/99, 105, 276; 127/30, 43, 54

[56] References Cited

U.S. PATENT DOCUMENTS 3,928,322 12/1975 Sugiyama ........................ 127/54 X
4,115,147 9/1978 Shimizu ................................ 127/54
4,277,563 7/1981 Kerkhoffs ........................ 435/105 X

*Primary Examiner*—Sidney Marantz
*Attorney, Agent, or Firm*—Sim & McBurney

[57] ABSTRACT

High fructose syrups are obtained from Jerusalem artichoke tubers and other naturally-occurring inulin-containing materials by extraction of the inulin and any related fructans from the tubers with water, elimination of some low molecular weight nitrogenous species and minerals from the aqueous extract by ultrafiltration, enzymatic hydrolysis of the inulin to fructose and glucose, separation of the reducing sugars from higher molecular species by ultrafiltration, and evaporative concentration of the purified reducing sugars solution to a syrup. The processing also removes colorants initially present in the aqueous extract. The dissolved solids in the syrup comprise at least 90 wt % reducing sugars and these sugars are constituted at least 60 wt %, often at least 75 wt %, by fructose with the balance glucose. The syrup is suitable for blending with 42 wt % fructose corn syrup to form the commercially-desirable 55 wt % fructose syrup and is obtained in much simpler and less expensive manner than conventional 80 to 90 wt % fructose corn syrup.

17 Claims, No Drawings

PRODUCTION OF HIGH FRUCTOSE SYRUP FROM INULIN INVOLVING ULTRAFILTRATION

FIELD OF INVENTION

The present invention relates to fructose manufacture.

BACKGROUND TO THE INVENTION

Fructose, in the form of corn syrup of high fructose content, has been increasingly used as a sweetener in the food industry, in view of the fact that it is 1.5 to 1.7 times sweeter than sucrose. Lower calorie products having the same sweetness can be produced when fructose is used as the sweetener as opposed to sucrose, glucose or maltose.

High fructose content corn syrups are conventionally derived from corn starch by a series of steps. In the first step, starch liquifaction and saccharification are effected using enzymatic and/or acid hydrolysis of the starch to yield a glucose containing syrup. Part of the glucose in the syrup then is isomerized to fructose, thereby forming a syrup containing reducing sugars in the weight proportions of about 42% fructose, 50% glucose and 8% higher saccharides. The latter syrup then is enriched and refined by fractionation to yield two products, namely a first syrup containing reducing sugars in the weight proportion of 90% fructose and 10% glucose and a second syrup containing reducing sugars in the weight proportion of 85% glucose and 15% higher saccharides.

There are three types of high fructose corn syrups available, namely one in which the reducing sugars comprise about 42 wt% fructose, which is produced by the hydrolysis and isomerization steps described above, one in which the reducing sugars comprise about 90 wt% fructose which is produced by fractionation of the 42 wt% fructose syrup as described above, and one in which the reducing sugars comprise about 55 wt% fructose which is produced by blending the 42 wt% fructose syrup and the 90 wt% fructose syrup in the required proportions.

The fractionation procedure which is used to form the 90 wt% syrup requires somewhat sophisticated technology and, as a result, the 90 wt% fructose syrup is an expensive material. Production of this material nevertheless is required to enable the 55 wt% fructose syrup, which is the fructose syrup most in demand by the food industry, to be produced by blending with the 42 wt% fructose syrup.

SUMMARY OF INVENTION

In accordance with the present invention, there is provided a process for the formation of a high purity syrup containing reducing sugars wherein fructose constitutes at least about 60 wt%, preferably about 75 to about 90 wt%, of the reducing sugars, in a much simplified and relatively inexpensive manner when compared with the prior art procedure noted above. The isomerization and fractionation steps of the prior art procedure are not required.

The present invention utilizes an inulin-containing naturally-occurring material, such as tubers of artichoke, Dahlia and chicory, as the starting material rather than corn containing starch. Certain cultivars of Jerusalem artichoke (*Helianthus tuberosus*), substantially outyield other sources of sweeteners, including corn and sugar beet, under Canadian prairie conditions, with production costs and production methods being comparable with those of potatoes.

The invention is described herein particularly with reference to tubers of Jerusalem artichoke. However, it will be understood that the principles thereof are applicable to any inulin-containing naturally-occurring material.

GENERAL DESCRIPTION OF INVENTION

The procedure of the present invention involves a multistep operation, generally as follows:

(1) Jerusalem artichoke tubers are extracted with water to dissolve inulin and related fructans therefrom, (2) the extract medium is subjected to ultrafiltration or other simultaneous concentration and purification procedure to retain the inulin and related fructans but to eliminate low molecular weight nitrogen-containing species, and minerals, (3) the retentate from the ultrafiltration, i.e. purified inulin and related fructans, is subjected to enzymatic hydrolysis to fructose and glucose, (4) the hydrolyzate is subjected to ultrafiltration or other simultaneous concentration and purification procedure to purify the fructose and glucose solution, and (5) the high purity filtrate is concentrated to a desired concentration, usually a syrupy consistency.

The initial extraction of the Jerusalem artichoke tuber is effected to solubilize the inulin and other related fructans from the tuber. The extraction is conveniently effected using water. Inulin is only sparingly soluble in water at temperatures below about 50° C. At higher temperatures, however, the solubility increases substantially, so that it is preferred to effect the solubilization at an elevated temperature above about 50° C., preferably about 80° to 90° C. The elevated temperature also increases the rate of solubilization of the inulin, inactivates any enzymes present which may interfere with later processing, and results in extraction of lower quantities of nitrogen-containing extractables.

The tuber may be sliced or cut into small portions to increase the surface area exposed to the extracting medium during solubilization. For ease of later filtration of solids from the aqueous solution resulting from the extraction, it is preferred to provide the subdivided tuber particles in as large a size as is commensurate with an acceptable level of extraction of inulin from the tuber. For tuber slices, it has been found that slice thicknesses below about 0.5 cm do not increase the extractability of inulin and hence it is preferred to utilize slices of about 0.5 to about 2 cm thick. For diced tubers, it has also been found that dimensions below about 0.5 cm do not increase the extractability of inulin and hence it is preferred to utilize diced tubers of about 0.5 cm to 1 cm size.

The chemical make up of the inulin in the tubers may vary depending on growth season and storage time. Usually the inulin and related fructans contain about 65 to 80 wt% fructose equivalents and the balance by weight of glucose equivalents.

In addition to the extraction of inulin and related fructans, lower molecular weight organic species, including low molecular weight nitrogen-containing material, for example, amino acids and peptides, and minerals also are extracted from the tubers. The size of the tuber particles and extraction temperature usually are controlled to maximize the extractability of inulin and fructans while minimizing the extraction of low molecular weight nitrogen-containing material and minerals, in accordance with the above discussion of these parameters.

Following completion of the extraction step, the resulting material is usually filtered to remove solid phase material, such as, soil and cell debris, from the aqueous inulin solution. The resulting filtered inulin solution usually contains coloured contaminants as well as the nitrogen-containing material and mineral species contamination. The filtration step may be effected at the elevated extraction temperature.

The filtered inulin solution then is subjected to a simultaneous concentration and purification step while amino acids, peptides, minerals and other contaminants of lower molecular weight than inulin and related fructans are removed from the solution. This simultaneous concentration and purification step may be effected by any convenient membrane technique whereby the contaminants are allowed to pass through the membrane with part of the aqueous phase while the inulin and related fructans are retained in the concentrated solution.

One convenient membrane technique which may be used in ultrafiltration although other techniques, such as, diafiltration, may be used. A membrane is chosen having the required molecular weight cut-off to achieve retention of the inulin and related fructans and passage of the lower molecular weight species. A molecular weight cut-off in the range of about 500 to about 2000 usually is employed. At the lower end of this range, a high yield of inulin and related fructans of low purity is obtained while, at the upper end of this range, a low yield of inulin and related fructans of high purity is obtained. A molecular weight cut-off of about 1000 has been found to provide a convenient balance of yield and purity.

The extent to which the inulin solution is concentrated depends upon purity and yield considerations. As the degree of concentration increases, the purity increases but the yield decreases as some fructans pass through the membrane. Preferably, the inulin solution is concentrated to about 5 to about 15% of its original volume.

When the desired concentration of the inulin solution with associated decrease of contaminants concentration has been effected, the concentrated inulin solution is subjected to enzymatic hydrolysis to break down the inulin and related fructans to fructose and glucose.

The enzymatic hydrolysis may be effected using inulase under any suitable conditions. The inulase which is used may be provided from any convenient source, for example it may be derived from yeasts, such as, *Candida kefyr* and *Kluyveromyces fragilis* (ATCC 12424). The production of inulase from the latter yeast is described in "Non-Specific B-Fructofuranosidase (Inulase) from *Kluyveromyces fragilis*", T. W. D. GrootWassink and S. E. Fleming, Enzyme and Microbial Technology, (1980) vol. 2 pp. 45 to 53. The inulase which is used in the enzymatic hydrolysis may also be derived from fungal sources, such as, *Aspergillus sp., Fusarium roseum* and *Penicillium sp.*, as described by L. Zitten, Proceedings of the 32nd Starch Convention of the Association of Cereal Research, held at Detmold, West Germany, 1981.

The enzymatic hydrolysis step results in a fructose solution which contains higher molecular weight species, including unhydrolyzed or only partially hydrolyzed inulin and related fructans, as well as the fructose, glucose and minor amounts of higher saccharides which are formed by hydrolytic breakdown of the inulin.

The fructose solution is purified to remove the higher molecular weight species by passing the solution through a membrane which retains the higher molecular weight species while permitting the fructose and glucose to pass therethrough. A molecular weight cut-off in the range of about 500 to about 1000 usually is used. The same ultrafiltration membrane as is used in the inulin solution concentration step may be used in the fructose solution purification step, although a membrane having a different molecular weight cut-off may be employed in the two procedures.

The extent to which the fructose solution is concentrated to provide the purified solution depends on purity and yield considerations. As the yield increases, the purity decreases due to the effects of concentration/equilibrium dynamics on non-fructose structures. Preferably, the hydrolysed solution is concentrated to about 30 to 35% of its original volume to provide the optimally purified fructose solution permeate.

The resulting purified fructose solution is an aqueous solution of solids which are in excess of 90 wt% reducing sugars, preferably at least 95 wt% reducing sugars and the balance protein and/or other species. The purified fructose solution usually is free or substantially free from colourants, which are removed in the two ultrafiltration steps.

The reducing sugars in the purified fructose solution usually comprise at least about 60 wt%, preferably about 75 to 90 wt%, fructose with the balance being glucose, depending on the relative proportions of equivalents of these substances in the starting material. The fructose solution may vary in color from water clear to light gold.

The fructose solution is obtained in relatively dilute form. In view of the limited solubility of inulin at temperatures below about 50° C., the concentration of inulin in the solution passing through the concentration step is generally quite low, resulting in a purified fructose solution having a solid concentration of less than about 5 wt%, preferably about 0.1 to about 3 wt%.

In instances where the membrane material permits the first ultrafiltration to be effected at an elevated temperature above about 50° C., much higher inulin concentrations are tolerable and, as a result, the purified fructose solution may have a solid concentration up to about 20 wt%.

The purified fructose solution is more dilute than is directly usable in making high (55%) fructose syrup, and the final step of the process, therefore, is a simple evaporative concentration by boiling, usually under a subatmospheric pressure, generally at a temperature of about 40° to 60° C. to avoid the sugar degradation which occurs at high temperatures, until a syrupy consistency is obtained, corresponding to a solids concentration usually in the range of about 70 to 80 wt%.

In the process of this invention, therefore, a high fructose syrup of very high fructose concentration is produced suitable for use in blending with 42 wt% fructose corn syrup to form 55 wt% fructose syrup. The product is obtained from an inexpensive crop and the processing steps are relatively simple and inexpensive when compared with the prior art procedures required to produce a 90 wt% fructose corn syrup.

EXAMPLES

EXAMPLE 1

This Example illustrates the application of the process of the invention to Jerusalem artichoke.

600 g of fall-harvested tubers of Jerusalem artichoke (*Helianthus tuberosus*) were washed and sliced. The slices were extracted in 12 liters of distilled water at 90° C. for fifteen minutes. The extract was cooled and filtered to remove dirt and cell debris. The extract had the following composition by weight (on a dry basis):

Protein (N×5.7): 8.4%
Ash: 4.6%
Reducing sugars (as fructose equivalent): 87.0%
Color: yellow-brown to brown 100 ml of the extract was introduced into the chamber of a batch-type stirred ultrafiltration cell (Amicon Model No. 202) fitted with a disc membrane (Amicon type no. UM-2) having a molecular weight cut-off of 1000. The extract sample was filtered under pressure (about 50 psi) until about 10% of the original volume remained in the cell. The filtrate fraction was discarded.

The retentate fraction was withdrawn from the cell, and the cell was washed with an equal volume of distilled water at 40° C. to remove any remaining inulin. The washed water was mixed with the retentate fraction, and the resulting mixture was subjected to enzymatic hydrolysis at 50° C. for 2 hours at a pH of 5 to 6 using 0.15 v/v inulase (from *Kluyveromyces fragilis*). The inulase was in the form of a preparation containing 1000 units/ml of extract wherein 1 unit liberates 1 g of hexose per min using sucrose as a substrate at pH 5 and 50° C.

After completion of the hydrolysis, the liquid phase was returned to the ultrafiltration cell and was filtered through the same membrane under pressure (50 psi) until about 30% of the volume remained in the cell. The retentate fraction was discarded.

The filtrate fraction was collected, had a dissolved solids concentration of 1.7% w/w and was found to have the following composition by weight (on a dry basis):

Protein (N×5.6): 2%
Ash: 0%
Reducing sugars as fructose equivalents: 98%
  fructose: 72% of the reducing sugars
  glucose: 28% of the reducing sugars
Color: water clear The product that was produced, therefore, consisted of high purity reducing sugars having a high proportion of fructose component, suitable for use, following concentration to a syrup, in blending with 42 wt% fructose corn syrup to form 55 wt% high fructose syrup.

Example 2

This Example illustrates the application of the process of the invention to Dahlia tubers.

An extract of Dahlia tubers (*Dahlia variabilis*) was prepared by contact of 600 g of tubers confined in cheesecloth bags with 12 liters of distilled water at 93° C. for 15 minutes. The extract solution was filtered to remove dirt and cell debris. The filtered extract had the following composition by weight (on a dry basis):

Protein (N×5.6): 3.8%
Ash: 11.1%
Reducing sugars (as fructose equivalents): 84.6%
Color: Dull green brown The extract was then subjected to the ultrafiltration, enzymatic hydrolysis and second ultrafiltration procedure described in Example 1 under identical conditions thereto, to result in filtrate from the second ultrafiltration having a dissolved solids concentration of 0.7% w/w and the following composition by weight (on a dry basis):

Protein (N×5.6): 1.4%
Ash: 4.0%
Reducing sugar (as fructose equivalent): 94.6%
Color: Water clear The product that was produced, therefore, consisted of a solution of high purity reducing sugars.

Example 3

This Example illustrates the utilization of an alternative ultrafiltration unit in the process of the invention as practised on Jerusalem artichoke.

Fall-harvested Jerusalem artichoke extract was prepared as described in Example 1, except that the tuber slices were contained in a cheesecloth bag during extraction. The extract was concentrated to 35 to 45 mg/ml sugar (measured as fructose equivalents) and then filtered to remove suspended solids.

Purification of a 200 ml extract was effected in a hollow fiber dialyzer/concentrator (Amicon Model No. DC2) fitted with a membrane having a molecular weight cut-off of 2000 (Amicon H1P2). The dialyzer/conentrator was run on the extract in the dialysis mode until about 2500 ml of distilled water had been flushed past at a pump speed of about 98 ml/min.

Enzymatic hydrolysis of the retentate was effected as described in Example 1 before being purified by running the dialyzer/concentrator in the concentration mode until about 20% of the volume remained. Analysis of the filtrate fraction, which had a dissolved solids concentration of 1.8% w/w, revealed the following composition by weight (on a dry weight basis):

Protein (N×5.6): 5%
Ash: 3%
Reducing sugars (as fructose equivalents): 92%
Color: clear light gold The light gold color and higher protein content indicate a lesser efficiency of purification than was achieved in Examples 1 and 2, but nevertheless the product was of acceptable purity for use, following concentration to a syrup, in blending with 42 wt% fructose corn syrup to form 55 wt% high fructose syrup.

Example 4

The procedure of Example 3 was repeated except that Dahlia tubers were substituted for Jerusalem artichoke. The composition by weight of the initial extract was (on a dry basis):

Protein (N×5.6): 3%
Ash: 9%
Reducing sugars (as fructose equivalents): 88%
Color: cloudy brown-green After purification, hydrolysis and repurification following the procedure of Example 3, the resulting sugar solution concentration 0.4% w/w had the following composition by weight (on a dry basis):

Protein (N×5.6): 3%
Ash: 6%
Reducing sugars: (as fructose equivalents) 91%
Color: clear gold As in the case of Example 3, the purity of the product sugar solution was less than in the case of Examples 1 and 2 but nevertheless was acceptable.

SUMMARY OF DISCLOSURE

In summary of this disclosure, the present invention produces a high fructose syrup in a simple inexpensive manner and in a form which can be readily blended with low fructose syrups from starch, e.g. corn starch, to form the commercially-desired 55 wt% fructose syrup. Modifications are possible within the scope of this invention.

What we claim is:

1. A process for producing a syrup containing reducing sugars wherein fructose constitutes at least 60 wt% of the reducing sugars, which comprises:

extracting soluble substances from an inulin-containing naturally-occurring material with water to form an aqueous inulin solution containing low molecular weight nitrogen-containing organic species and minerals, simultaneously concentrating said aqueous inulin solution and removing at least a substantial proportion of said low molecular weight nitrogen-containing organic species and minerals therefrom to form a concentrated inulin solution by a membrane technique which permits said lower molecular weight nitrogen-containing organic species and minerals to pass through the membrane while retaining said inulin in solution, subjecting said concentrated inulin solution to enzymatic hydrolysis to form fructose and glucose from inulin and any related fructans present in said concentrated inulin solution to produce a fructose solution containing unhydrolyzed and partially hydrolyzed higher molecular weight species, removing at least a substantial proportion of said higher molecular weight species from said fructose solution to form a purified fructose solution containing reducing sugars of at least about 90 wt% of the dissolved material therein and wherein fructose constitutes at least about 60 wt% of said reducing sugars, said removal being effected by a membrane technique which permits fructose and glucose to pass therethrough to form said fructose solution while retaining said higher molecular weight species, and evaporatively concentrating said purified fructose solution to a syrup of desired concentration.

2. The process of claim 1 wherein said water extraction is effected at an elevated temperature of above about 50° C., said inulin-containing material is in comminuted form during said extraction, and said aqueous inulin solution is filtered to remove suspended solids therefrom prior to said first-mentioned concentration step.

3. The process of claim 2 wherein said elevated temperature is above 80° to about 90° C.

4. The process of claim 1 wherein said enzymatic hydrolysis is effected using inulase.

5. The process of claim 1 wherein said membrane technique used to remove said higher molecular weight species is effected using an ultrafiltration membrane having a molecular weight cut-off of about 500 to about 1000.

6. The process of claim 1 wherein said evaporative concentration is effected under a subatmospheric pressure and at a temperature of about 40° to about 60° C. to form a syrup having solid concentration of about 70 to 80 wt%.

7. The process of claim 1 wherein said reducing sugars comprise at least about 95 wt% of the dissolved solids of said fructose syrup and fructose constitutes about 75 to 90 wt% of said reducing sugars.

8. The process of claim 1 wherein said membrane technique used in said concentration of inulin solution is effected using an ultrafiltration membrane having a molecular weight cut-off of about 500 to about 2000.

9. The process of claim 8 wherein said molecular weight cut off is about 1000.

10. The process of claim 1, 2, 3, 8, 5, 6 or 7 wherein said inulin-containing material is Jerusalem artichoke tubers.

11. A process for producing a syrup containing dissolved solids constituted at least about 95 wt% by reducing sugars of which at least about 75 wt% is constituted by fructose and the balance glucose, from Jerusalem artichoke tubers, which comprises:

slicing said tubers to provide a plurality of exposed tuber surfaces, extracting inulin and related fructans along with other water-soluble substances from said sliced tubers by contact with water at a temperature of about 80° to about 90° C. to form an inulin-containing solution, filtering said inulin-containing solution to remove suspended solids therefrom, subjecting the resulting filtered inulin solution to a first ultrafiltration step to retain inulin and related fructans in a retentate and to expel at least a substantial proportion of said other water-soluble substances in a filtrate, enzymatically hydrolyzing the inulin and related fructans in said retentate using inulase to form a reducing sugar solution containing higher molecular weight species, subjecting said reducing sugar solution to a second ultrafiltration step to expel said reducing sugars, constituted at least 75 wt% by fructose and the balance glucose, as a filtrate to form a purified fructose solution having dissolved solids constituted at least 90 wt% by said reducing sugars and to retain at least a substantial proportion of said higher molecular weight species as a retentate, and evaporatively concentrating said purified fructose solution by boiling under a subatmospheric pressure at a temperature below about 60° C. to form said syrup.

12. The process of claim 11 wherein said first ultrafiltration step is effected using a membrane having a molecular weight cut-off of about 500 to about 2000.

13. The process of claim 11 wherein said purified fructose solution has a solid concentration of below about 20 wt% and said evaporative concentration is effected to form a syrup having a solid concentration of greater than about 70 wt%.

14. The process of claim 11 wherein said tuber slices have a thickness of about 0.5 to about 2 cm.

15. The process of claim 14 wherein said molecular weight cut-off is about 1000.

16. The process of claim 11, 14 or 12 wherein said second ultrafiltration step is effected using a membrane having a molecular weight cut-off of about 500 to about 1000.

17. The process of claim 11, 14 or 12 wherein said second ultrafiltration step is effected using a membrane having a molecular weight cut-off of about 500 to about 1000, said purified fructose solution has a solids concentration of below about 20 wt%, and said evaporative concentration is effected at a temperature of about 40° to about 60° C. to form a syrup having a solid concentration of greater than about 70 wt%.

* * * * *